United States Patent [19]
Iwamoto et al.

[11] Patent Number: 5,811,242
[45] Date of Patent: Sep. 22, 1998

[54] MARKER AND REAGENT FOR DIABETES MELLITUS AND DIABETES MELLITUS COMPLICATION

[75] Inventors: Hisahiko Iwamoto; Masato Okada, both of Tokuyama, Japan

[73] Assignee: Tokuyama Corporation, Yamaguchi-ken, Japan

[21] Appl. No.: 735,240

[22] Filed: Oct. 22, 1996

[30] Foreign Application Priority Data

Oct. 24, 1995 [JP] Japan ..................... 7-275514
Mar. 25, 1996 [JP] Japan ..................... 8-068631

[51] Int. Cl.$^6$ .................... G01N 33/53; G01N 33/72; G01N 33/543; C07K 16/00
[52] U.S. Cl. .................. 435/7.1; 435/7.93; 435/7.94; 435/7.54; 435/975; 435/7.92; 435/962; 530/388.1; 530/387.5; 530/389.3; 530/391.3; 530/391.7; 436/66; 436/67
[58] Field of Search ................. 435/7.1, 7.54, 435/7.93, 7.94, 962, 975, 7.92; 530/388.1, 389.3, 387.5, 389.1, 391.3, 391.7; 436/66, 67

[56] References Cited

U.S. PATENT DOCUMENTS

| | | |
|---|---|---|
| 5,202,424 | 4/1993 | Vlassaia et al. . |
| 5,223,392 | 6/1993 | Cahen . |
| 5,316,754 | 5/1994 | Vlassaia et al. . |
| 5,366,859 | 11/1994 | Miyoshi et al. . |
| 5,610,076 | 3/1997 | Founds et al. . |
| 5,624,804 | 4/1997 | Bucala . |
| 5,629,408 | 5/1997 | Bucala . |
| 5,683,887 | 11/1997 | Bucala . |
| 5,712,101 | 1/1998 | Bucala . |

OTHER PUBLICATIONS

Monnier et al., "Relation Between Complications Of Type I Diabetes Mellitus And Collagen–Linked Fluorescence", *The New England Journal Of Medicine*, vol. 314, No. 7, pp. 403–408, Feb. 13, 1986.

Morisaki et al., "AGE And Diabetes Complications", Saishin Igaku, vol. 49, pp. 248–254, 1994.

Ahmed et al., "Identification Of N$^\epsilon$–Carboxymethyllysine As A Degradation Product Of Fructoselysine In Glycated Protein", *The Journal of Biological Chemistry*, vol. 261, No. 11, pp. 4889–4894, 1986.

Dunn et al., "Age–Dependent Accumulation of N$^\epsilon$–(Carboxymetyl)Lysine And N$^\epsilon$–(Carboxymethyl) Hydroxylysine In Human Skin Collagen", *Biochemistry*, vol. 30, pp. 1205–1210, 1991.

Reddy et al., "Carboxymethyllysine Is A Major Antigenic Determinant In AGE–Proteins", *Abstract of the 55th U.S. Diabetes Mellitus Academic Society's Meeting*, p. 115A, 1995.

Monnier et al Nephrol Dial Transplant 11[Suppl 5]:20–26, 1996.

Requena et al, Nephrol Dial Transplant 11 [Suppl 5]:48–53, 1996.

Reddy et al, 55th US Diabetes Millitus Academic Society's Mtg p. 115A Abstract 431, 1995.

Makita et al, IBC 267/8:5133–38, 1992.

Radoff et al, Diabetes; 40/12:1731–38, 1991.

Vlassaia et al, PNAS, vol. 82:5588–5592, 1985.

Skolnik et al, J. Exp. Med. 174:931–939, 1991.

Makita et al Science, 258:651–653, 1992.

Edwards et al Clinica Chimica Acta, 104:161–67, 1980.

Yang et al, J. Exp. Med. 174: 1991.

Radoff et al Arch. Biochem & Biophys. 263/2:418–423, 1988.

Bucala et al, Mol. Immunol 20/12:1289–1292, 1983.

Radoff et al. Diabetes 39: 1510–1518, 1990.

Kirstein et al, PNAS 87:9010–9014, 1990.

Cerami et al J. Cellular Biochem. 30:111–120, 1986.

Horuichi et al, JBC 266/12:7329–7332, 1991.

Nakazama et al J. Immunol Methods. 140:119–125, 1991.

Mitsuhashi et al, Diabetes 42:826–832, 1993.

Nakayama et al, Diabetes 42:345–350, 1993.

*Primary Examiner*—Nita Minnifield
*Attorney, Agent, or Firm*—Wenderoth, Lind & Ponack, L.L.P.

[57] ABSTRACT

N$^\epsilon$-carboxymethyllysine, a carboxymethylated protein in which at least part of the side-chain amino groups of amino acid residues constituting the protein is carboxymethylated, or a carboxymethylated peptide in which at least part of the side-chain amino groups of amino acid residues constituting the peptide is carboxymethylated can be used as a marker for diabetes mellitus or diabetes mellitus complications.

9 Claims, 1 Drawing Sheet

MARKER AND REAGENT FOR DIABETES MELLITUS AND DIABETES MELLITUS COMPLICATION

DETAILED DESCRIPTION OF THE INVENTION

This invention relates to a marker and a reagent for diabetes mellitus and diabetes mellitus complications. More particularly, it relates to a marker for the diagnosis of diabetes mellitus and diabetes mellitus complications and for the evaluation of the medicinal effect of a medicine and to a reagent for the diagnosis, treatment or prevention of diabetes mellitus and diabetes mellitus complications.

It is known that a protein in the blood reacts with glucose non-enzymatically to be glycated and becomes a glycated protein. The glycation is called "Maillard reaction" and is divided into former-stage and latter-stage reactions. The former-stage reaction is generally defined as a stage that the side-chain amino group or N-terminal amino group of the protein reacts with a carbonyl group of sugar to produce Amadori rearranged compounds via a Schiff base. As the former-stage reaction products are known hemoglobin A1C, glycated albumin and the like, and it is known that they are used as a clinical marker for diabetes mellitus.

It is also known that, after the above former-stage reaction, the produced Amadori rearranged compounds are changed in two directions. One of them is a reaction accompanied by at least one of fluorescence, browning and crosslinking in the molecule or/and between molecules (also referred to as "latter-stage reaction A" hereinafter) and the other is an oxidative cleavage reaction (also referred to as "latter-stage reaction B" hereinafter) in which oxygen and a transition metal are involved.

Although the final product of the Maillard reaction may be called "AGE" (Advanced Glycation End products), the term "AGE" generally refers to the product of a reaction accompanied by at least one of three characteristic phenomena (fluorescence, browning and crosslinking in the molecule or/and between molecules) which are seen in the above latter-stage reaction A. Opinion may be divided on whether or not the products of a reaction not accompanied by all the above three phenomena should also be referred to as AGE. That is, in addition to the above definition, there are various opinions on the definition of AGE, such as one asserting that AGE should refer to all the products obtained when glucose and protein are incubated in vitro at 37° C. for 60 days or more (a model reaction of the Maillard reaction), one asserting that AGE should refer only to products having biological activity to cause diabetes mellitus complications, and the like. There is no established definition of the term at the academic society. To avoid the above confusion, when the term "AGE" is used in this specification, it refers only to the product of a reaction (namely, the product of the latter-stage reaction A) accompanied by at least one of the characteristics of fluorescence, browning or crosslinking in the molecule or/and between molecules in the Maillard reaction.

The product of the above latter-stage reaction A, that is, AGE, is considered to be a mixture of many different compounds. At present, pyrraline, pentosidine, closslines A&B, X1 and the like are proposed as AGE structures and are qualitatively and quantitatively determined by the measurement of fluorescence intensity or an antigen-antibody reaction. It is reported that the latter-stage reaction A for generating AGE takes place in vivo and is connected with the occurrence of a complication based on vascular dysfunction (Monnier, V. M., et al, New England Journal of Medicine, vol.314, p.403, 1986), and attention is being paid to AGE as being connected with the occurrence and progress of complications in diabetes mellitus patients. It is also reported that AGE has biological activity related to the occurrence and progress of diabetes mellitus complications (Morisaki et al, "Saishin Igaku", vol.49, p.248, 1994).

Meanwhile, $N^\epsilon$-carboxymethyllysine (may be abbreviated as CML hereinafter) is identified as the product of the other reaction in the latter stage of the Maillard reaction (latter-stage reaction B) (Ahmed, M. U., et al, Journal of Biological Chemistry, vol.261, p.4889, 1986), and it is reported that CML is present in the lens proteins and skin collagen of the aged and diabetes mellitus patients (Dunn, J. A., et al, Biochemistry, vol.30, p.1205, 1991). It is also reported that a substance in which a hydrogen atom of the side-chain amino groups of bovine serum albumin (to be sometimes abbreviated as BSA hereinafter) is substituted with carboxymethyl groups (may be referred to as "carboxymethylated" hereinafter) greatly inhibits a reaction between AGE and an anti-AGE antibody (the Abstract of the 55-th US Diabetes Mellitus Academic Society's Meeting, p.115A, 1995).

However, there is no report on the biological activity of the product of the latter-stage reaction B. The difference in the concentration of the product of the latter-stage reaction B in vivo, particularly in a body fluid, between a case of diabetes mellitus or complications of it, such as nephropathy or retinopathy (may be referred to as "case of a diabetes mellitus complication" hereinafter) and that of a healthy person has been unknown, and the utility of the product, particularly, utility as a marker for diabetes mellitus or diabetes mellitus complications has not been recognized. That is, although the utility of AGE as a marker for diabetes mellitus or diabetes mellitus complications is being made clear, the utility of CML, a carboxymethylated protein or carboxymethylated peptide (may be simply referred to as "CML or the like" hereinafter) as a marker for diabetes mellitus or diabetes mellitus complications has not been recognized. Further, it has been unknown whether these substances are the causes of diabetes mellitus complications or substances accumulated by diabetes mellitus complications.

It is therefore an object of the present invention to confirm that CML or the like has the same biological activity as that of AGE.

It is another object of the present invention to confirm that there is observed a significant difference in the concentration of CML or the like in vivo, particularly in a body fluid, between a case of diabetes mellitus or a case of diabetes mellitus complications and that of a healthy person.

It is a further object of the present invention to verify that CML or the like can be used as a marker for diabetes mellitus or diabetes mellitus complications based on the above confirmation, that is, to provide CML or the like as a marker for diabetes mellitus or diabetes mellitus complications.

It is a still further object of the present invention to provide a reagent for diagnosis of diabetes mellitus or diabetes mellitus complications, which reacts with CML or the like in a body fluid immunologically.

The above and other objects and advantages of the present invention will become more apparent from the following description.

According to the present invention, firstly, the above objects and advantages of the present invention can be attained by using as a marker for diabetes mellitus or diabetes mellitus complications one member selected from the group consisting of N$^\epsilon$-carboxymethyllysine, a carboxymethylated protein in which at least part of the side-chain amino groups of amino acid residues constituting the protein is carboxymethylated and a carboxymethylated peptide in which at least part of the side-chain amino groups of amino acid residues constituting the peptide is carboxymethylated.

Secondly, the above objects and advantages of the present invention can be attained by an immunological reagent for the diagnosis of diabetes mellitus or diabetes mellitus complications or for the evaluation of the medicinal effect, which is composed of at least one member selected from the group consisting of an antibody which reacts specifically with N$^\epsilon$-carboxymethyllysine, an antibody which reacts specifically with a carboxymethylated protein in which at least part of the side-chain amino groups of amino acid residues constituting the protein is carboxymethylated and an antibody which reacts specifically with a carboxymethylated peptide in which at least part of the side-chain amino groups of amino acid residues constituting the peptide is carboxymethylated.

Figure 1:
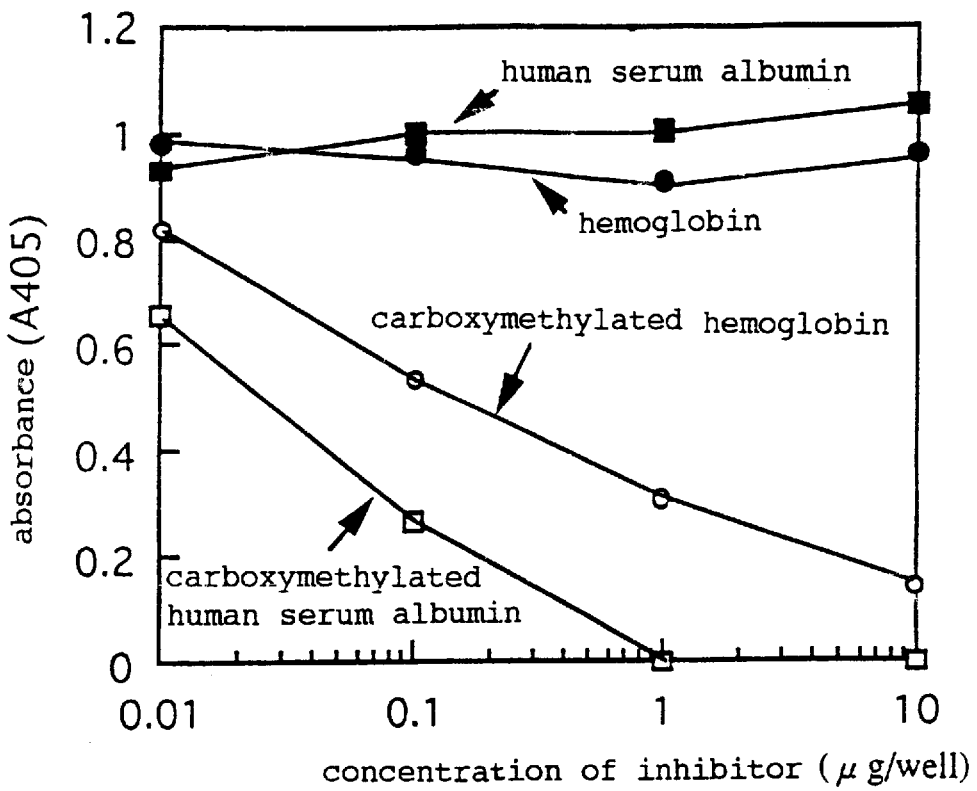
FIG. 1 is a graph showing the measurement results of the antigen specificity of an antibody against a prepared carboxymethylated human serum albumin with a competitive ELISA, in which the axis of ordinate shows absorbance at 405 nm and the axis of abscissa shows the amount of each inhibitor.

The present invention will be described in detail hereinunder. A description is first given of a marker.

The protein used in the present invention is not limited to a particular one and may be a protein derived from a body fluid or tissue.

Illustrative examples of the protein include simple proteins such as albumin, $\beta_2$ microglobulin, histone and prolamin; glycoproteins such as collagen, $\gamma$-globulin and erythrocyte peripheral membrane proteins; lipoproteins such as low-density lipoproteins and high-density lipoproteins; conjugated proteins such as metal proteins including hemoglobin, transferrin and ceruloplasmin.

The peptide used in the present invention is not limited to a particular one and may be an oligopeptide or polypeptide, as exemplified by products obtained by the decomposition of the above proteins, products obtained by artificially synthesizing a specific area of the above proteins, and products synthesized from protein precursors by limited hydrolysis. The peptide is preferably a product obtained by degradation of a protein derived from a blood fluid or tissue.

As a method for carboxymethylating the side-chain amino group of amino acid constituting the above protein or peptide or the side-chain amino group of lysine (may be referred to as "carboxymethylation" hereinafter), that is, as a method for substituting the hydrogen of the above amino group with a group —CH$_2$—COOH can be used any of known methods without restriction. For example, like a reduction alkylation method described in "Shin Seikagaku Jikken Koza, Tanpakushitsu 4 (New Biochemical Experiment Lecture 1, Protein 4)" (pp.13–16, edited by the Japanese Biochemical Society and published by Tokyo Kagaku Dojin on Mar. 20, 1991), a method is preferred in which an aldehyde compound such as glyoxylic acid (CHO—COOH) and a protein or peptide are dissolved in an aqueous solution such as a borate buffer solution or phosphate buffer solution and are allowed to react with each other at a pH value of 8 to 10 in the presence of a hydrogenation reducing agent such as sodium borohydride or sodium cyanoborohydride. At a pH value higher than 10, the protein or the like may be denatured, while at a pH value lower than 8, the hydrogenation reducing agent becomes unstable. To proceed the reaction specifically and quantitatively, the reaction temperature is preferably at a temperature of 0° to 10° C. The thus obtained carboxymethylated protein or carboxymethylated peptide is generally water-soluble and precipitates by the addition of acetone, alcohol, ammonium sulfate, heavy metal salt or the like. The above carboxymethylated protein or carboxymethylated peptide can be detected by a known method other than a method for detecting an amino group, such as an ultraviolet absorption method, dye-binding assay, phenol reagent method or the like. In the above methods, a substance having an amino group such as protein, lipid, sugar or the like is easily carboxymethylated, whereas, in the protein or peptide, the amino groups of the side chain of lysine or N-terminal amino acid residue are apt to be carboxymethylated selectively. Particularly, only one amino group of the N-terminal is present in one molecule of a protein or peptide, while a plurality of side-chain amino groups of lysine are contained in the molecule in many cases. Therefore, to introduce a large number of carboxymethyl groups into the protein or peptide, the amino acid constituting the protein or peptide is preferably lysine.

Although carboxymethyllysine (CML) may be obtained from lysine as a starting material by carboxymethylation as described above, it may be obtained by hydrolyzing the carboxymethylated protein or carboxymethylated peptide obtained by the above method, using a strong acid.

CML or the like obtained by the above method is purified by dialysis, centrifugal concentration, liquid chromatography or the like, and then measured for its biological activity.

Whether CML or the like can be used as a marker for the diagnosis of diabetes mellitus or diabetes mellitus complications or for the evaluation of a medicinal effect can be judged from whether the occurrence of diabetes mellitus complications such as nephropathy, retinopathy, arteriosclerosis, neurosis or the like occurs when CML or the like obtained by the above method is caused to act on a living organism or bio component. For instance, CML or the like is allowed to act on a model cell to measure its coagulation ability which is related with the occlusion of the capillary vessel which is one of the causes of nephropathy or arteriosclerosis, its permeability which is related with the occurrence and progress of retinopathy, and the like (Morisaki et al, "Saishin Igaku", vol.49, pp.248, 1994).

To measure the coagulation ability, the activity of thrombomodulin of the endothelium having fibrinolytic activity, for example, may be measured. For measurement of the above activity, a known method comprising allowing a carboxymethylated protein to act on the endothelium, adding thrombin and protein C and measuring the produced active protein C is used without problem.

To measure the permeability, the amount of the carboxymethylated protein taken up into the endothelium may be measured, and a known method comprising adding the labelled carboxymethylated protein to the endothelium, incubating the protein and measuring the amount of the carboxymethylated protein taken up into the endothelium is used.

Figure 2:
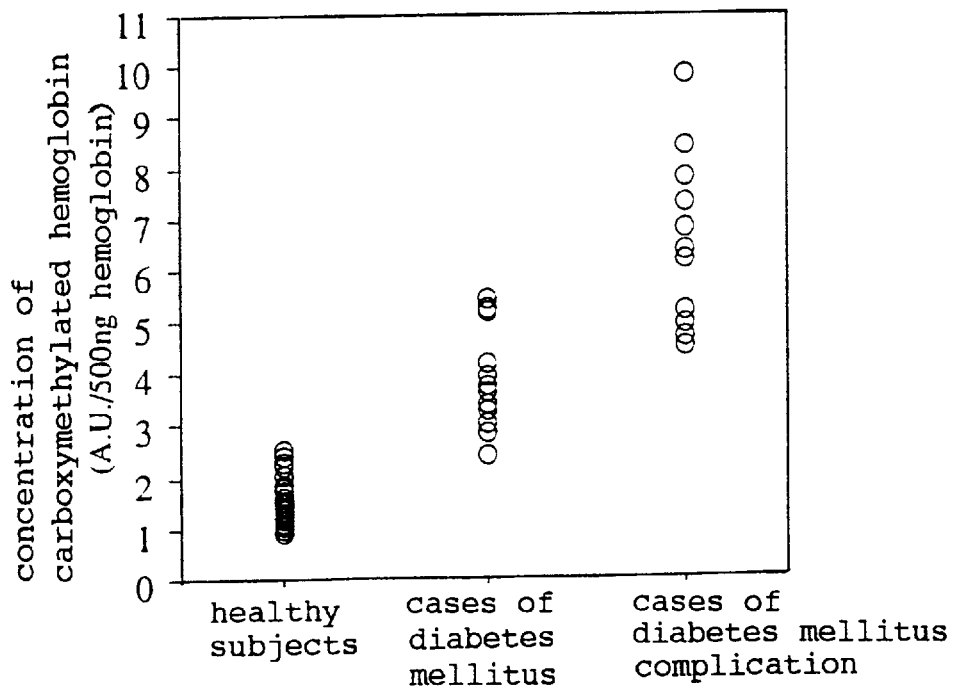
FIG. 2 is a graph showing the concentrations of carboxymethylated hemoglobin in the blood of a healthy person, a case of diabetes mellitus and a case of diabetes mellitus complications.

As shown in Examples to be described hereinafter, CML or the like used in the present invention shows biological activity in the above measurement. Further, since the concentration of CML or the like present in the body of a case of diabetes mellitus or diabetes mellitus complications is significantly higher than that of a healthy person (see FIG. 2), CML or the like used in the present invention can be used as a marker for diabetes mellitus or diabetes mellitus complications in the field of clinical diagnosis. That is, it is made possible to judge whether a patient is affected by diabetes mellitus or estimate the progress of diabetes mellitus and the possibility of the occurrence of diabetes mellitus complications by measuring the concentration of CML or the like contained in a tissue such as kidney glomerulus or collagen, or a body fluid such as urine, blood or the like.

Diabetes mellitus may be either insulin-dependent or non-dependent, and diabetes mellitus complications include nephropathy, retinopathy, arteriosclerosis and neurosis.

The term "marker" as used in the present invention denotes both a marker for diagnosis and a marker for the evaluation of a medicinal effect.

A method for measuring the concentration of CML or the like in vivo (such as the concentration of a carboxymethylated protein in the blood or urine) is not particularly limited, and any of known methods for detecting CML or the like may be employed. Examples of the detection method include one for detecting a carboxymethylated protein or carboxymethylated peptide in vivo through an antigen-antibody reaction, one for detecting CML or the like with liquid chromatography, one for detecting CML with liquid chromatography/mass spectrometry by hydrolyzing carboxymethylated proteins or carboxymethylated peptides, one for detecting CML with gas chromatography/mass spectrometry by hydrolyzing carboxymethylated proteins or carboxymethylated peptides, and the like.

Out of these, according to the present invention, there is provided an immunological reagent for the diagnosis of diabetes mellitus or diabetes mellitus complications or the evaluation of the medicinal effect, which is composed of at least one member selected from the group consisting of an antibody which reacts specifically with $N^\epsilon$-carboxymethyllysine, an antibody which reacts specifically with a carboxymethylated protein in which at least part of the side-chain amino groups of amino acid residues constituting the protein is carboxymethylated and an antibody which reacts specifically with a carboxymethylated peptide in which at least part of the side-chain amino groups of amino acid residues constituting the peptide is carboxymethylated, as described above.

The antibody which reacts specifically with CML as used in the present invention denotes an antibody which binds specifically to the carboxymethyl group-substituted hydrogen of the side chain amino group of lysine or lysine derivative. An antigen for raising the antibody, that is, an immunogen may be carboxymethylated lysine or lysine derivative. Since the above lysine or lysine derivative has extremely low ability to induce immune response, CML bonded to a conventionally known carrier protein such as hemocyanin, bovine serum albumin, β-galactosidase or the like is preferably used as an immunogen to form an antibody. To bind the lysine or lysine derivative to a carrier protein, a method used for this purpose is generally used without restriction.

The antibody which reacts specifically with the carboxymethylated protein or the antibody which reacts specifically with the carboxymethylated peptide denote antibodies which bind specifically to a protein or peptide having an N-carboxymethylated side-chain amino group. An antigen for raising the antibody, that is, an immunogen may be a protein or peptide having an N-carboxymethylated side-chain amino group such as a N-carboxymethyllysine group.

The antibody raised using such antigen is not particularly limited. An antiserum, ascites or the like obtained by immunizing host animals such as a rabbit, goat, mouse or guinea pig with an antigen is used directly or as a polyclonal antibody through purification by a conventionally known method such as a salting-out method, gel filtration method, ion exchange chromatography, affinity chromatography or electrophoresis. Further, a monoclonal antibody prepared from a hybridoma obtained by fusing an antibody producing cell such as a spleen cell or lymphocyte of a mammal immunized by an antigen with a myeloma cell can be used directly or through purification by a conventionally known method such as a salting-out method, gel filtration method, ion exchange chromatography, affinity chromatography or electrophoresis.

The antibody thus obtained may be used as an anti-CM antibody or an active fragment (portion including an antigen-recognition site of the antibody) of an antibody obtained by treating the above antibody with enzyme, such as Fab, Fab' or F(ab')2, may be used as an anti-CM antibody.

The term "anti-CM antibody" denotes an antibody which reacts specifically with carboxymethyllysine, an antibody which reacts specifically with the above carboxymethylated protein or an antibody which reacts specifically with the above carboxymethylated peptide.

The term "immunological reagent" of the present invention denotes a labelling immunoassay reagent for detecting an antigen-antibody reaction caused by making an insoluble carrier carry an anti-CM antibody, antibody against a bio component(s) or antigen in a specimen and bringing it into contact with an antigen in the specimen or an anti-CM antibody, by colorimetric analysis, luminescence assay, fluorescence assay or the like, or an immunoagglutination reagent for detecting the reaction by making use of the agglutination of the insoluble carrier.

Illustrative examples of a qualitative reagent include a latex agglutination reagent, microtiter agglutination reagent and the like, whereas illustrative examples of a quantitative reagent include radioimmunoassay reagent, enzyme immunoassay reagent, fluorescent immunoassay reagent, latex quantitative reagent and the like.

As for the form of the insoluble carrier carrying the anti-CM antibody or the antibody against a bio component (s), or the antigen in the specimen, a suitable form may be selected according to application purpose. For example, it may be in a form of bead, test plate, disk or filter, or in a spherical or tubular form. As the material of the above antibody or carrier may be used ones which are generally used as an immunoassay carrier, such as glass, polysaccharide and derivatives thereof, silica gel, porous ceramics, metal oxides, erythrocyte, synthetic resins such as propylene, styrene, acrylamide and acrylonitrile, and these synthetic resins having a reactive functional group(s) such as a sulfone group and amino group introduced thereinto by a known method.

As a method for immobilizing an anti-CM antibody or antibody against a bio component(s) or an antigen in a specimen to the insoluble carrier may be used known methods such as a physical adsorption method, covalent binding method, ionic binding method, crosslinking method and the like without restriction.

As the antibody to be carried on the insoluble carrier is used the anti-CM antibody or the antibody against a bio component(s). Illustrative examples of the antibody against a bio component(s) include anti-albumin antibody, anti-hemoglobin antibody, anti-γ-globulin antibody, anti-low-density lipoprotein antibody, anti-transferrin antibody, anti-erythrocyte peripheral membrane protein antibody and the like. As the antibody against a bio component(s) may be used an antibody against only one bio component or an antibody against two or more bio components. When an antibody against a bio component(s) is carried on the insoluble carrier, it may be contacted to an anti-CM antibody after it is contacted to an antigen in a specimen. When an anti-CM antibody is carried on the insoluble carrier, it may be contacted to the anti-CM antibody again after it is brought into contact with an antigen in a specimen.

The basic measurement operation of CML or the like with a labelling immunoassay reagent can be conducted in accordance with a conventional detection method such as radio-imunoassay (RIA), enzyme immunoassay (EIA) or the like. The operation and procedure in each of the above detection methods do not differ from those generally employed and can be based on a known non-competitive method, competitive method, sandwich method or the like.

For instance, the anti-CM antibody or antibody against a bio component(s) or the antigen in the specimen is carried on the insoluble carrier in a proportion of 0.01 to 1,000 $\mu g/cm^2$ and brought into contact with 0.001 to 1,000 $\mu g$ of the anti-CM antibody or the antigen in the specimen for measurement. When the anti-CM antibody or antibody against a bio component(s) is carried on the insoluble carrier, it is brought into contact with an anti-CM antibody after it is contacted to the antigen in the specimen, as described above. The anti-CM antibody which is not carried on the insoluble carrier is preferably used an antibody labelled with a labelling agent.

Illustrative examples of the labelling agent include radioactive substances such as radioactive iodine and radioactive carbon; fluorescent substances such as fluorescein isothiocyanate and tetramethyl rhodamine; enzymes such as alkaline phosphatase and peroxidase; and the like. The antigen-antibody complex obtained by the above method is detected by colorimetric analysis, fluorescence assay, luminescence assay or the like.

The basic measurement operation of CML or the like with an immunoagglutination reagent can be based on a conventional detection method such as a hemaagglutination, passive agglutination, nephelometric immunoassay, turbidimetric immunoassay or the like. The operation and procedure of each of the detection methods can follow those generally employed.

For instance, particles (to be referred to as "sensitized particles" hereinafter) carrying 0.001 to 100 mg of an anti-CM antibody per 1 g of it may be used as an effective component of an immunological reagent by dispersing in an aqueous medium so that it is contained in an amount of 0.001 to 15% by weight. The average particle diameter of the insoluble carrier carrying the antibody is preferably 0.05 to 10 $\mu m$ from a view point of easy occurrence of agglutination after the antigen-antibody reaction and easy judgment of the agglutination. The sensitized particles prepared by the above method are brought into contact with an antigen in a specimen to measure the degree of agglutination of the sensitized particles. The degree of agglutination of the particles can be measured visually or by a known optical measurement or other conventional method without restriction.

Using the above immunoassay methods, the immunological reagent for diabetes mellitus or diabetes mellitus complications of the present invention can be advantageously used as a reagent for the diagnosis of diabetes mellitus or diabetes mellitus complications or a reagent for the evaluation of the medicinal effect for the treatment or prevention of diabetes mellitus or the treatment or prevention of diabetes mellitus complications.

When the reagent of the present invention is used as a diagnostic reagent, the proportion of an antigen in a specimen, that is, CML or the like contained in a specific bio component(s) is measured using an anti-CM antibody. Illustrative examples of the bio component include body fluids such as blood, urine, lymph, amniotic fluid, cerebrospinal liquid and saliva; tissues such as skin collagen, lens proteins, artery and kidney; and the like. A body fluid often used as a specimen for clinical diagnosis is preferred.

When the reagent of the present invention is used as a reagent for the evaluation of a medicinal effect, a reduction in the proportion of CML or the like contained in a specific bio component(s) is measured by administering a medicine for the treatment of diabetes mellitus or diabetes mellitus complications.

An antibody against CML or the like is obtained by a conventional method for immunizing a rabbit with human serum albumin containing CML or the like. This antibody reacts significantly with various glycated proteins prepared in vitro but not with a non-glycated protein. Further, the antibody also reacts with human hemoglobin, and it reveals that a case of diabetes mellitus or a case of diabetes mellitus complications reacts more significantly with the antibody than a healthy person. An antibody against CML or the like and AGE exhibit immunological cross-reactivity. It is obvious from the results of various studies that a case of diabetes mellitus is placed under higher oxygen stress than a healthy person. CML or the like formed by a glycation and an oxidation reaction is extremely useful as a new marker for the diagnosis of the occurrence and progress of diabetes mellitus complications.

As described above, since it has been made clear that CML or the like used in the present invention is related with the occurrence and progress of diabetes mellitus complications, it is obvious that the CML or the like can be used as a novel clinical marker for diabetes mellitus or diabetes mellitus complications in the field of clinical diagnosis. This indicates the possibility of constructing a new diagnostic system which makes use of the above novel marker in the diagnosis of diabetes mellitus or diabetes mellitus complications and has great industrial significance. Further, use of the immunological reagent of the present invention which uses an antibody against CML or the like (anti-CM antibody) makes it possible to diagnose diabetes mellitus and diabetes mellitus complications from a body fluid or tissue as a specimen with ease. Further, a diagnostic reagent prepared by the present invention can be used for the evaluation of the medicinal effect of a medicine for the treatment of diabetes mellitus and a medicine for the treatment of diabetes mellitus complications.

The following examples are provided for the purpose of further illustrating the present invention but are in no way to be taken as limiting.

Example 1

To carboxymethylate the side-chain amino group of a protein, 1 ml of a human serum albumin solution (Fraction V, a product of Sigma Co. Ltd.) having a pH value of 9 and a concentration of 1 mg/ml was mixed with 1 ml of 0.25M glyoxylic acid (manufactured by Sigma Co. Ltd.) having a pH value of 9 and left to stand at 0° C. for 12 hours. Thereafter, 1 mg of sodium cyanoborohydride was added to the resulting mixture and left to stand for another 12 hours.

As a control, human serum albumin was treated in the same manner as above except that glyoxylic acid was not added.

The carboxymethylation rates of the above treated human serum album were obtained by measuring unreacted amino groups by the following method using trinitrobenzene-sulfonic acid (to be abbreviated as TNBS hereinafter).

That is, 0.5 ml of each sample was added to 0.5 ml of a 0.1M sodium hydroxide aqueous solution containing 0.1M sodium tetraborate. Thereafter, 20 μl of 1.1M TNBS recrystallized and washed with diluted hydrochloric acid was added to the above solution and stirred. After 30 minutes, 2 ml of 98.5 mM sodium dihydrogen phosphate containing 1.5 mM sodium sulfide was added to terminate the reaction. After diluting 1:10 in water, the absorbance at 420 nm was measured. The absorbance of carboxymethylated human serum albumin was found to be 0.03 and the absorbance of human serum albumin which was not treated with glyoxylic acid was found to be 1.25. When a system containing no human serum album was measured in the same manner, the absorbance was 0.03. Therefore, it was found that the carboxymethylation rate of carboxymethylated human serum album was 100%.

The carboxymethylated human serum albumin obtained by the above method was dialyzed with a 20 mM phosphate buffer solution (pH: 7.4) at 4° C. for 2 days to remove unreacted glyoxylic acid and sodium cyanoborohydride and then measured for the activity of thrombomodulin to examine the hypercoagulability, that is, the progress of the occlusion of the vessel. This measurement was carried out as follows.

The above carboxymethylated human serum albumin was added to the semiconfluent human arterial endothelial cells (obtained from Dainippon Pharmaceutical Co. Ltd.) so as to have a concentration of 10 μM and incubated at 37° C. for 20 hours. After this incubation, the endothelial cells were washed with an Earl's balanced salt solution, thrombin was added so as to have a concentration of 1 U/ml, protein C was added so as to have a concentration of 1 mg/ml, and the endothelial cells was further incubated at 37° C. for 15 minutes. Antithrombin III was added to this culture solution containing the endothelial cells to terminate the formation of active protein C, and a substrate composed of lysine-proline-arginine-paranitroanilide was added so as to have a concentration of 1 mM. The absorbance at 405 nm was measured 5 minutes and 10 minutes after the addition and then, the difference between these absorbances was obtained. The difference of absorbance per 1 mg of a protein derived from the endothelial cells was 60% for the carboxymethylated human serum albumin when the difference of absorbance obtained in Comparative Example 1 described later was taken as 100%.

This means that the carboxymethylated human serum albumin reduces the activity of thrombomodulin by 40% and this in turn induces the occlusion of the vessel due to a reduction in fibrinolytic activity, that is, the hypercoagulability. Since AGE obtained in Reference Example 1 reduces the activity of thrombomodulin by 80% as shown in Reference Example 1 described later, it is obvious that this carboxymethylated human serum albumin has a capability to induce the occlusion of the vessel like the AGE.

Comparative Example 1

Human serum albumin (control) which was not treated with glyoxylic acid prepared in Example 1 was dialyzed in the same manner as in Example 1 and measured for the activity of thrombomodulin in the same manner as in Example 1. The difference between absorbances after 5 minutes and after 10 minutes was 0.915, and this value was taken as 100%.

Reference Example 1

60 mg of human serum albumin and 1.7M glucose were added to 1 ml of a 0.5M phosphate buffer solution (pH: 7.4), filtrated with a 0.45 μm filter, sterilized and left to stand at 37° C. for 3 months to obtain AGE (fluorescence, browning and crosslinking in the molecule or between molecules were observed). The activity of thrombomodulin was measured in the same manner as in Example 1 except that the AGE obtained by the above method was used in place of the carboxymethylated human serum albumin.

As a result, the relative ratio of the absorbance difference based on the thrombomodulin activity of the above AGE was 20% when the absorbance difference obtained in Comparative Example 1 was taken as 100%. This means that the AGE reduces the thrombomodulin activity by 80%.

Example 2

To carboxymethylate the side-chain amino group of human transferrin which is a protein, 1 ml of a human transferrin solution (produced by Wako Pure Chemical Industries, Ltd.) having a concentration of 1 mg/ml and a pH value of 9 was mixed with 1 ml of 0.25M glyoxylic acid (produced by Sigma Co. Ltd) having a pH value of 9, and the mixture was left to stand at 0° C. for 12 hours. Thereafter, 1 mg of sodium cyanoborohydride was added and the resulting mixture was left to stand for another 12 hours. As a control, human transferrin was treated in the same manner except that glyoxylic acid was not added.

The above carboxymethylated human transferrin and human transferrin not treated with glyoxylic acid were each diluted with an aqueous solution consisting of 0.2 ml of Bio-Lyte (pH range of 3 to 10, a product of BIO-RAD Co. Ltd.), 3 ml of glycerol and 6.8 ml of distilled water to 5 times and each 10 μl fraction of the diluted solution was used for isoelectric focusing electrophoresis. The isoelectric focusing electrophoresis was carried out with a commercial gel having a pH range of 3 to 10 (manufactured by Tefco Co. Ltd.) at 100 V for 30 minutes, 200 V for 30 minutes and 500 V for 60 minutes, using 0.05M sodium hydroxide as a catholyte and 0.01M phosphoric acid as an anolyte. As the result of the electrophoresis, the isoelectric point of the carboxymethylated human transferrin was 4.6 to 4.9 and that of the human transferrin not treated with glyoxylic acid was 5.2 to 5.5. This result shows that acarboxymethyl group was introduced into the side-chain amino group of human transferrin by the above carboxymethylation.

The carboxymethylated human transferrin obtained by the above method was dialyzed with a 20 mM phosphate buffer solution (pH: 7.4) at 4° C. for 2 days to remove unreacted glyoxylic acid and sodium cyanoborohydride. The amount taken up by monocyte was determined in order to measure its permeability (related to the occurrence and progress of retinopathy). The uptake amount was measured by the following method.

$2 \times 10^5$ cells of strain RAW 264.7 derived from the murine monocyte, were seeded into each well of a 12-hole plate and incubated at 37° C. for 18 hours in RPMI medium containing 10% of fetal bovine serum. After removing the culture medium, the cells were washed with a phosphate buffer solution once and transferred to 1 ml of DMEM medium containing 3% of BSA. After 1 hour of incubation at 37° C., carboxymethylated human transferrin labelled with 125I was added so as to have a concentration of 10 μM and the cells were further incubated at 37° C. for 12 hours. The carboxymethylated human transferrin labelled with 125I was prepared by adding 5 μl of an Na 125I aqueous solution containing 0.5 m Ci to 10 μl of a solution containing 2.5 μg of carboxymethylated human transferrin and carrying out a reaction for 15 minutes. After 12 hours of incubation, the cells were washed with a phosphate buffer solution containing 1% BSA three times and further with a phosphate buffer solution three times. After the addition of 1 ml of a 0.1M sodium hydroxide solution and 1 hour of incubation at 37° C., the cells were scraped off and measured for their radioactivity with a scintillation counter. 0.4 μg of the carboxymethylated human transferrin was taken up into the murine monocyte per 1 mg of a protein derived from the murine monocyte. As shown in Comparative Example 2 to be described hereinafter, the human transferrin which was not carboxymethylated was not taken up into the monocyte, whereas the carboxymethylated human transferrin was taken up into the monocyte. Therefore, it has been made clear that the carboxymethylated human transferrin induces permeability into the monocyte which is related with the occurrence and progress of retinopathy.

It is obvious from the result of Reference Example 2 described later that the carboxymethylated human transferrin of this example induces permeability into the monocyte like AGE obtained in Reference Example 1.

Comparative Example 2

After the human transferrin which was not treated with glyoxylic acid obtained in Example 2 as a control was dialyzed in the same manner as in Example 2, the amount of the human transferrin taken up into the monocyte was measured in the same manner as in Example 2. It was found that the amount of human transferrin taken up per 1 mg of a protein derived from the murine monocyte was 0.05 μg or less.

Reference Example 2

The uptake amount of AGE was measured in the same manner as in Example 2 except that AGE obtained in Reference Example 1 was used in place of the carboxymethylated human transferrin. As a result, the amount of AGE taken up per 1 mg of a protein derived from the murine monocyte was 1.0 μg.

Example 3

(1) Raising of antibody against carboxymethylated protein

A rabbit weighing 2 kg or more was immunized by the carboxymethylated human serum albumin prepared in Example 1 as an antigen in the following manner.

A mixture containing 0.5 ml of the antigen solution having a concentration of 2 mg/ml and 0.5 ml of Freund's complete adjuvant was injected into the ear vein of a rabbit. Thereafter, a mixture containing 0.25 ml of the antigen solution having a concentration of 2 mg/ml and 0.25 ml of Freund's incomplete adjuvant was additionally injected every two weeks. During this time, to confirm whether an antibody against carboxymethylated human serum albumin was produced, blood was partially drawn from the marginal ear vein of the rabbit once every two weeks. After six weeks, it was confirmed by an ELISA method that the antibody against the carboxymethylated human serum albumin was produced and all the blood was drawn.

(2) Preparation of affinity purification column 25 ml of Affi-gel 15 (manufactured by BIO-RAD Co. Ltd) was washed with 75 ml of 10 mM acetate buffer (pH: 4.5), and 62.5 ml of a human serum albumin solution having a concentration of 10 mg/ml was added and stirred gently at room temperature for 1 hour. Thereafter, unreacted human serum albumin was removed by filtration, 30 ml of 1M ethanolamine was added and stirred gently at room temperature, and unreacted N-hydroxysucciimide ester was blocked. A carrier having the human serum albumin immobilized was packed into a column and washed with ion exchange water until the absorbance thereof at 280 nm became 0. Further, the column was equilibrated with 20 mM phosphate buffered saline (pH: 7.4).

(3) Affinity purification of antibody against carboxymethylated human serum albumin The thus prepared antibody against carboxymethylated human serum albumin was diluted with 20 mM phosphate buffered saline (pH: 7.4) so as to have a concentration of 1 mg/ml, and the diluted antibody was applied to the affinity purification column in an amount of about 100 mg. Thereafter, the phosphate buffer solution was flown at a flow rate of 0.5 ml/min until the absorbance at 280 nm became 0. The antibody which failed to bind to the column was collected as an antibody against carboxymethylated human serum albumin. When the absorbance at 280 nm became 0, the phosphate buffer solution was exchanged with 0.1M glycine buffer (pH: 3.0), the antibody bound to the column was eluted, and the column was equilibrated with 20 mM phosphate buffered saline (pH:7.4). The collected antibody was applied to the column again, and the antibody not bound to the column was collected. This operation was repeated one more time and the antibody was used as an antibody for labelling biotin.

(4) Biotin labelling of antibody against carboxymethylated human serum albumin

Biotin was labelled with the thus purified antibody, using a Protein Biotinylation System kit (manufactured by Gibco Co. Ltd.).

To a solution prepared by diluting or concentrating the purified antibody against carboxymethylated human serum albumin with 20 mM phosphate buffered saline (pH: 7.4) so as to have a concentration of 1.5 mg/ml was added sodium carbonate buffer (pH: 9.0) so as to have a concentration of 0.05M. Thereafter, to 6.7 ml of this antibody solution was added 26 μl of a CAB-NHS ester solution having a concentration of 50 mg/ml which was prepared in accordance with the instruction manual, and stirred gently at room temperature for 1 hour. Ammonium chloride was further added to a concentration of 0.11M to terminate a reaction. Subsequently, the antibody solution was desalted in a column provided with this kit. Further, when the number of moles of biotin introduced by Avidin/HABA provided with the kit was calculated, it was found that 14 moles of biotin were bound per 1 mole of the antibody against carboxymethylated human serum albumin.

(5) Antigen specificity of antibody against carboxymethylated human serum albumin The antigen specificity of the antibody against carboxymethylated human serum albumin was confirmed by competitive ELISA.

To the antibody against carboxymethylated human serum albumin which was diluted with 10 mM phosphate buffered saline (pH: 7.4) (to be abbreviated as PBS hereinafter) so as to have a concentration of 1 μg/ml was added the prepared carboxymethylated human serum albumin so as to have concentrations of 0.1, 1, 10 and 100 μg/ml. Each of these solutions was left at 37° C. for 1 hour and used as an antibody solution inhibited by the carboxymethylated human serum albumin.

Carboxymethylated hemoglobin produced from hemoglobin (manufactured by Sigma Co. Ltd) was prepared in the same manner as in the preparation of the carboxymethylated human serum albumin. The carboxymethylated hemoglobin was added to the antibody solution against the carboxymethylated human serum albumin having a concentration of 1 μg/ml so as to have concentrations of 0.1, 1, 10 and 100 μg/ml. Each of these solutions were left at 37° C. for 1 hour and used as an antibody solution inhibited by the carboxymethylated hemoglobin.

Before the competitive ELISA was carried out, the prepared carboxymethylated human serum albumin was diluted with PBS so as to have a concentration of 1 μg/ml. Thereafter, the diluted carboxymethylated human serum albumin solution was applied to a 96-hole immunoplate (manufactured by NUNC Co. Ltd) in an amount of 100 μl per 1 well and left at 37° C. for 1 hour to immobilize the carboxymethylated human serum albumin on the immunoplate. After 1 hour, the carboxymethylated human serum albumin which failed to bind to the immunoplate was removed, and PBS containing 0.5% of gelatin was applied to the immunoplate in an amount of 100 μl per 1 well and left at 37° C. for 1 hour to block a portion of the immunoplate to which the carboxymethylated human serum albumin was not bound. After 1 hour, the gelatin solution was removed, the immunoplate was washed with PBS three times, and the antibody solution inhibited by the carboxymethylated human serum albumin having each of the above concentrations or the antibody solution inhibited by the carboxymethylated hemoglobin having each of the above concentrations was applied to the immunoplate in an amount of 100 μl per 1 well and left at 37° C. for 1 hour. Thereafter, the immunoplate was washed with PBS three times, and a solution of an anti-rabbit IgG antibody labelled with alkaline phosphatase having a concentration of 1 μg/ml (manufactured by Cosmobio Co. Ltd) was applied in an amount of 100 μl per 1 well and left at 37° C. for 1 hour. Further, the immunoplate was washed with PBS three times, and a substrate solution prepared in accordance with the instruction manual of an alkaline phosphatase substrate kit (a product of BIO-RAD Co. Ltd.) was applied in an amount of 100 μl per 1 well. After it was left at room temperature for 5 minutes, 100 μl of a 0.4M sodium hydroxide solution was added per 1 well to terminate the reaction of alkaline phosphatase and measure absorbance at 405 nm. The measured absorbances are shown in Table 1 and the results are shown in FIG. 1. It is suggested from the results that the prepared antibody against the carboxymethylated human serum albumin is also reactive with the carboxymethylated hemoglobin because a reaction between the carboxymethylated human serum albumin and the antibody not only by the carboxymethylated human serum albumin but also by the carboxymethylated hemoglobin.

TABLE 1

Measurement results of antigen specificity of antibody against carboxymethylated human serum albumin

| Antigen | Concentration of inhibitor (μg/well) | Absorbance (A405) |
| --- | --- | --- |
| Human serum albumin | 0.01 | 0.93 |
| | 0.1 | 0.997 |
| | 1 | 1.004 |
| | 10 | 1.052 |
| Carboxymethylated human serum albumin | 0.01 | 0.656 |
| | 0.1 | 0.267 |
| | 1 | 0 |
| | 10 | 0 |
| Hemoglobin | 0.01 | 0.98 |
| | 0.1 | 0.963 |
| | 1 | 0.911 |
| | 10 | 0.96 |
| Carboxymethylated hemoglobin | 0.01 | 0.816 |
| | 0.1 | 0.536 |
| | 1 | 0.308 |
| | 10 | 0.141 |

(6) Measurement of carboxymethylated hemoglobin in diabetes mellitus patients

The red blood cells in 50 μl of blood drawn from each of 15 cases of diabetes mellitus which did not suffer from complications by a vacuum blood-collecting tube containing EDTA-2K was washed with 250 μl of saline once and hypotonically lysed by addition of 1 ml of distilled water to obtain a specimen. The average age of the cases was 55.7.

Carboxymethylated hemoglobin contained in the specimen was measured by a dot blotting method. After the concentration of hemoglobin was measured by a cyanmethemoglobin method, hemoglobin was adsorbed to a PVDF filter (manufactured by BIO-RAD Co. Ltd) in an amount of 500 ng using a dot blotting apparatus (manufactured by BIO-RAD Co. Ltd). The filter was blocked by 10% skimmed milk in PBS (pH: 7.4) at room temperature for 1 hour and then incubated with 1 μg/ml of biotin-labelled antibody against carboxymethylated human serum albumin in PBS. After 1 hour of incubation at room temperature, the filter was washed with 50 ml of PBS containing 0.05% of Tween 20 (pH: 7.4) three times. Thereafter, to the filter was added 5 ml of a complex of avidin and biotin labelled with peroxydase (Vectastine ABC Kit of Funakoshi K. K.) and incubation was carried out at room temperature for 1 hour. The filter was washed with a 20 mM phosphate buffer solution containing 0.05% of Tween 20 (pH: 7.4) three times and 2 ml of an ECL western blotting detection reagent (a product of Amasham Co. Ltd) was added. The detection of luminescent intensity in the filter was carried out using the BIO-RAD GS-363 Molecular Imager.

As a control, carboxymethylated hemoglobin was measured by the same method as described above using commercial hemoglobin (manufactured by Sigma Co. Ltd) as a specimen. The measurement results are shown in Table 2. The luminescent intensity of hemoglobin derived from the above case of diabetes mellitus is plotted in FIG. 2 in which one specimen corresponds to one open circle when the luminescent intensity of the commercial hemoglobin is 1.

TABLE 2

Measurement results of carboxymethylated hemoglobin in blood derived from cases of diabetes mellitus

| Specimen No. | Luminescent intensity |
| --- | --- |
| 1 | 2145 |
| 2 | 1731 |
| 3 | 2012 |
| 4 | 2150 |
| 5 | 2145 |
| 6 | 2703 |
| 7 | 1935 |
| 8 | 1853 |
| 9 | 1546 |
| 10 | 2673 |
| 11 | 2790 |
| 12 | 1690 |
| 13 | 1229 |
| 14 | 1664 |
| 15 | 1449 |
| Control 1) | 512 |

Note
1): The specimen is commercial hemoglobin.

Example 4

Carboxymethylated hemoglobin contained in a specimen was measured in accordance with the method of Example 3 except blood obtained from each of 12 cases of diabetes mellitus complications who suffered from nephropathy or retinopathy in addition to diabetes mellitus was used as the specimen in place of blood derived from the case of diabetes mellitus. The measurement results are shown in Table 3. The average age of the cases was 56.5. As in Example 3, the luminescent intensity of hemoglobin derived from the above cases of diabetes mellitus complications is plotted in FIG. 2 in which one specimen corresponds to one open circle when the luminescent intensity of the commercial hemoglobin is 1.

TABLE 3

Measurement results of carboxymethylated hemoglobin in blood derived from cases of diabetes mellitus complication

| Specimen No. | Luminescent intensity |
| --- | --- |
| 1 | 2534 |
| 2 | 3466 |
| 3 | 3256 |
| 4 | 3174 |
| 5 | 2657 |
| 6 | 4306 |
| 7 | 3732 |
| 8 | 5033 |
| 9 | 3261 |
| 10 | 3983 |
| 11 | 2417 |
| 12 | 2299 |
| Control 1) | 512 |

Note
1): The specimen is commercial hemoglobin.

Comparative Example 3

Carboxymethylated hemoglobin contained in a specimen was measured in accordance with the method of Example 3 except blood obtained from each of 47 healthy subjects was used as the specimen in place of blood derived from the case of diabetes mellitus. The measurement results are shown in Table 4. The average age of the cases was 52.3. As in Example 3, the luminescent intensity of hemoglobin derived from the above healthy subjects is plotted in FIG. 2 in which one specimen corresponds to one open circle when the luminescent intensity of the commercial hemoglobin is 1.

TABLE 4

Measurement results of carboxymethylated hemoglobin in blood derived from healthy subjects

| Specimen No. | Luminescent intensity |
| --- | --- |
| 1 | 660 |
| 2 | 732 |
| 3 | 937 |
| 4 | 773 |
| 5 | 1126 |
| 6 | 1060 |
| 7 | 1285 |
| 8 | 1178 |
| 9 | 640 |
| 10 | 742 |
| 11 | 609 |
| 12 | 543 |
| 13 | 538 |
| 14 | 548 |
| 15 | 548 |
| 16 | 486 |
| 17 | 881 |
| 18 | 1224 |
| 19 | 502 |
| 20 | 773 |
| 21 | 681 |
| 22 | 799 |
| 23 | 722 |
| 24 | 911 |
| 25 | 568 |
| 26 | 604 |
| 27 | 707 |
| 28 | 522 |
| 29 | 937 |
| 30 | 886 |
| 31 | 650 |
| 32 | 655 |
| 33 | 758 |
| 34 | 599 |
| 35 | 568 |
| 36 | 568 |
| 37 | 573 |
| 38 | 691 |
| 39 | 814 |
| 40 | 814 |
| 41 | 471 |
| 42 | 471 |
| 43 | 558 |
| 44 | 594 |
| 45 | 681 |
| 46 | 732 |
| 47 | 937 |
| Control 1) | 512 |

Note
1): The specimen is commercial hemoglobin.

When the luminescent intensities of the group of cases of diabetes mellitus measured in Example 3 are compared with those of healthy subjects statistically (it test), the luminescent intensities of the group of cases of diabetes mellitus were much higher than those of healthy subjects with a significant difference (p<0.0 5). This means that blood derived from a case of diabetes mellitus contains much more carboxymethylated hemoglobin than blood derived from a healthy subject.

When the luminescent intensities of the group of cases of diabetes mellitus complications measured in Example 4 were compared with those of a group of healthy subjects by the t test, the luminescent intensities of the group of cases of diabetes mellitus complications are much higher than those of the group of healthy subjects with a significant difference (p<0.05). This means that blood derived from a case of a diabetes mellitus complication contains much more carboxymethylated hemoglobin than blood derived from a healthy subject.

It is made clear from the above results that CML or the like is useful as a marker for diabetes mellitus or diabetes mellitus complications.

Further, when the luminescent intensities of the group of cases of diabetes mellitus measured in Example 3 are compared with the group of cases of diabetes mellitus complications measured in Example 4 by the t test, the luminescent intensities of the group of cases of diabetes mellitus complications are much higher than those of the group of diabetes mellitus with a significant difference (p<0.05) 5%. This makes it clear that CML or the like is useful as a clinical marker for judging the progress of diabetes mellitus and the possibility of the occurrence of diabetes mellitus complications.

What is claimed is:

1. A method of using carboxymethylated hemoglobin as a marker for diabetes mellitus or diabetes mellitus complications, which comprises detecting, in the blood from a patient, a carboxymethylated hemoglobin in which at least part of the side-chain amino acid residues constituting the hemoglobin are carboxymethylated.

2. The method of claim 1, wherein the marker is used for diagnosis or the evaluation of a medicinal effect.

3. The method of claim 1, wherein the diabetes mellitus is either insulin dependent or insulin non-dependent.

4. The method of claim 1, wherein the diabetes mellitus complications are nephropathy, retinopathy, arteriosclerosis and neurosis.

5. An immunological reagent for the diagnosis of diabetes mellitus or diabetes mellitus complications, which is an antibody specifically reacting with a carboxymethylated hemoglobin in which at least part of the side-chain amino acid residues constituting the hemoglobin are carboxymethylated.

6. An immunological reagent for diagnosis of claim 5, which is in the form of a member selected from the group consisting of a latex agglutination reagent, microtiter agglutination reagent, radioimmunoassay reagent, enzyme immunoassay reagent and fluorescent immunoassay reagent.

7. An immunological reagent for the evaluation of the medicinal effect of a medicine for treatment or prevention of diabetes mellitus or diabetes mellitus complications, which is an antibody specifically reacting with a carboxymethylated hemoglobin in which at least part of the side-chain amino acid residues constituting the hemoglobin are carboxymethylated.

8. An immunological reagent for the evaluation of a medicinal effect of claim 7, which is in the form of a member selected from the group consisting of a latex agglutination reagent, microtiter agglutination reagent, radioimmunoassay reagent, enzyme immunoassay reagent and fluorescent immunoassay reagent.

9. An immunological method for the diagnosis of diabetes mellitus or diabetes mellitus complications, which comprises reacting a carboxymethylated hemoglobin in which at least part of the side-chain amino acid residues constituting the hemoglobin are carboxylated with an antibody specifically reacting with said carboxymethylated hemoglobin in blood.

* * * * *

UNITED STATES PATENT AND TRADEMARK OFFICE
CERTIFICATE OF CORRECTION

PATENT NO.  : 5,811,242
DATED       : September 22, 1998
INVENTOR(S) : Hisahiko Iwamoto et al.

It is certified that error appears in the above-indentified patent and that said Letters Patent is hereby corrected as shown below:

Column 17, line 26, after "side-chain" insert --amino groups of--.

Column 18, line 4, after "side-chain" insert --amino groups of--;

line 16, after "side-chain" insert --amino groups of--; and line 28, after "side-chain" insert --amino groups of--.

Signed and Sealed this

Twenty-seventh Day of July, 1999

Attest:

Q. TODD DICKINSON

*Attesting Officer*  *Acting Commissioner of Patents and Trademarks*